(12) United States Patent
Gottschalk-Gaudig

(10) Patent No.: US 8,586,639 B2
(45) Date of Patent: *Nov. 19, 2013

(54) RHEOLOGY CONTROL OF PICKERING EMULSIONS BY ELECTROLYTES

(75) Inventor: Torsten Gottschalk-Gaudig, Mehring (DE)

(73) Assignee: Wacker Chemie AG, Munich (DE)

( * ) Notice: Subject to any disclaimer, the term of this patent is extended or adjusted under 35 U.S.C. 154(b) by 2063 days.

This patent is subject to a terminal disclaimer.

(21) Appl. No.: 11/573,379

(22) PCT Filed: Jul. 28, 2005

(86) PCT No.: PCT/EP2005/008248
§ 371 (c)(1),
(2), (4) Date: Feb. 7, 2007

(87) PCT Pub. No.: WO2006/018112
PCT Pub. Date: Feb. 23, 2006

(65) Prior Publication Data
US 2007/0209552 A1    Sep. 13, 2007

(30) Foreign Application Priority Data
Aug. 12, 2004 (DE) .................. 10 2004 039 212

(51) Int. Cl.
| B01J 13/00 | (2006.01) |
|---|---|
| B01F 17/00 | (2006.01) |
| B01F 17/54 | (2006.01) |
| C08L 83/04 | (2006.01) |
| C09J 11/04 | (2006.01) |
| A61K 9/113 | (2006.01) |
| A61K 8/06 | (2006.01) |
| A61K 8/25 | (2006.01) |
| A61K 8/34 | (2006.01) |
| C08L 101/12 | (2006.01) |

(52) U.S. Cl.
USPC .......... 516/22; 516/23; 516/54; 516/55; 516/924; 524/588; 510/417; 106/287.1; 514/938; 514/939

(58) Field of Classification Search
USPC .......... 516/54, 55, 22, 23, 924; 524/588; 514/938, 939; 510/417; 106/287.1
See application file for complete search history.

(56) References Cited

U.S. PATENT DOCUMENTS

| 1,963,065 | A | * | 6/1934 | Auer et al. .............. 554/26 |
|---|---|---|---|---|
| 5,643,555 | A | | 7/1997 | Collin |
| 5,686,054 | A | * | 11/1997 | Barthel et al. ............. 423/335 |
| 5,851,715 | A | * | 12/1998 | Barthel et al. ............. 430/108.3 |
| 6,585,983 | B1 | | 7/2003 | Gers-Barlag et al. |
| 7,722,891 | B2 | | 5/2010 | Barthel et al. |
| 2003/0017531 | A1 | | 1/2003 | Werner et al. |
| 2003/0175221 | A1 | | 9/2003 | Gers-Barlag et al. |
| 2003/0175317 | A1 | | 9/2003 | Barthel et al. |
| 2004/0127580 | A1 | | 7/2004 | Baran, Jr. |
| 2004/0131527 | A1 | * | 7/2004 | Gottschalk-Gaudig et al. ............. 423/335 |
| 2004/0241120 | A1 | | 12/2004 | Pataut et al. |
| 2005/0266055 | A1 | * | 12/2005 | Stiller et al. ............. 424/443 |
| 2007/0281878 | A1 | * | 12/2007 | Gottschalk-Gaudig et al. ............. 510/417 |

FOREIGN PATENT DOCUMENTS

| CN | 1449862 A | 10/2003 |
|---|---|---|
| DE | 198 42 787 A1 | 3/2000 |
| DE | 102 38 649 A1 | 3/2004 |
| EP | 1526153 A1 * | 4/2005 |
| JP | 08169808 A | 7/1996 |
| JP | 2003-311144 A1 | 11/2003 |
| JP | 2006515308 A | 5/2006 |
| WO | WO 02/096378 A1 | 12/2002 |
| WO | WO 2005/092989 A1 | 10/2005 |

OTHER PUBLICATIONS

Derwent Abstract, week 200761, London: Derwent Publications Ltd., AN 2004-238922, DE 10238649 A, (Beiersdorf AG), abstract.*
Derwent Abstract, week 201016, London: Derwent Publications Ltd., AN 2005-758305, 2005092989 A1, (Wacker Chem AG), abstract.*
Derwent Abstract, week 200780, London: Derwent Publications Ltd., AN 2000-273047, DE 19842787 A1, (Beiersdorf AG), abstract.*
B. P. Binks et al, "Transitional Phase Inversion of Solid-Stabilized Emulsions Using Particle Mixtures", Langmuir, 2000, 16, 3748-3756 (Published on web Mar. 2000).*
B. P. Binks and S. O. Lumsdon, "E.ects of oil type and aqueous phase composition on oil-water mixtures containing particles of intermediate hydrophobicity", Phys. Chem. Chem. Phys., 2000, 2, 2959-2967 (Published on web Jun. 2000).*
B. R. Midmore and T.M. Herrington, "Silica-stabilised multiple emulsions", Progr Colloid Polym Sci (1999) 112: 115-120 (Obtained online @ http://www.springerlink.com/content/y321qkn2f50rwaa9 (downloaded Mar. 25, 2010).*
B.P. Binks et al., "Temperature-dependent stability of water-in-undecanol emulsions", Colloids and Surfaces A: Physicochem. Eng. Aspects vol. 224, Issues 1-3, (Aug. 29, 2003) 241-249, obtained online @ http://www.sciencedirect.com/ (downloaded Sep. 11, 2010).*
Derwent Abstract, week 200039, London: Derwent Publications Ltd., AN 1996-021697, JP 08169808 A, (L'Oreal SA), abstract.*
Derwent Abstract, week 200672, London: Derwent Publications Ltd., AN 2004-516935, JP 2006515308 A, (3M Innovative Properties Co), abstract.*

(Continued)

Primary Examiner — Daniel S Metzmaier
(74) Attorney, Agent, or Firm — Brooks Kushman P.C.

(57) ABSTRACT

Oil-in-water emulsions contain an oil dispersed phase, an aqueous continuous phase, and partly silylated pyrogenic silica having a content of silanol groups of 1.7 to 0.9 SiOH/$nm^2$ wherein 50% to 95% of silanol groups of the starting silica are silylated, present at the interface between the dispersed phase and the continuous phase and an electrolyte content in the aqueous phase which establishes the viscosity of the emulsion.

16 Claims, No Drawings

(56) References Cited

OTHER PUBLICATIONS

Lagaly et al., "Dispersionen und Emulsionen", Steinkopff, Darmstadt 1997, p. 1-4.

English Abstract for Lagaly et al., "Dispersionen und Emulsionen" Darmstadt 1997, p. 1-4.

De Rooij et al., "Steady Shear Viscosity of Weakly Aggregation Polystyrene Latex Dispersions", J. Chem. Phys. Dec. 1, 1993, 99, p. 9213.

Papirer et al., "Inverse Gaschromatography"—"Characterisation of Polymers and other materials", 391 ACS Symposium Series, Chapter 18, pp. 248-261, (1989 ©).

Sears, G. W., "Determination of Specific Surface Area of Colloidal Silica by Titration with Sodium Hydroxide" Anal. Chem, vol. 28, No. 12, (1956), p. 1981.

Washburn, E. W., "The Dynamics of Capillary Flow", Physical Review, vol. 17, No. 3, (1921), p. 273.

Schoelkopf et al., Journal of Colloid and Interface Science, vol. 227, (2000), pp. 119-131.

English Abstract corresponding to Lucas R., "Über das Zeitgesetz des kapillaren Aufstiegs von Flüssigkeiten", Koll. Journal 23, 15 (1918).

Lucas R., "Über das Zeitgesetz des kapillaren Aufstiegs von Flüssigkeiten", Koll. Journal 23, 15 (1918).

\* cited by examiner

RHEOLOGY CONTROL OF PICKERING EMULSIONS BY ELECTROLYTES

CROSS-REFERENCE TO RELATED APPLICATION

This application is the U.S. national phase of PCT Appln. No. PCT/EP2005/008248 filed Jul. 28, 2005 which claims priority to German application 10 2004 039 212.9 filed Aug. 12, 2004.

BACKGROUND OF THE INVENTION

1. Field of the Invention

The invention relates to the use of electrolytes for controlling the flow properties of emulsions of the oil-in-water (O/W) type.

2. Description of the Related Art

Emulsions as oil-in-water (O/W) dispersions are widely used as an application form for coating materials, such as, for example, water-based paints and finishes, as adhesives and sealants, such as, for example, aqueous epoxy or polyurethane systems, as cosmetic formulations, as cleansing agents and disinfectants, in the food industry, for the surface modification of solid substrates or as reaction media in emulsion polymerization.

In general, the dispersing and stabilization of the disperse phase are effected with the aid of emulsifiers. Cationic, anionic, ampholytic and nonionic emulsifiers are used. Common to the emulsifiers is that they are surface-active substances. That is to say, they preferably accumulate at interfaces, such as, for example, liquid-liquid, liquid-solid or liquid-gas interfaces, and thus reduce the interfacial/surface energy. On application of the emulsion, however, the emulsifiers can also cover the surface of the substrate to be treated and thus greatly change the wetting properties of the surface. This can adversely affect, for example, the adhesion properties of a coating material or of an adhesive joint or seal. Furthermore, the recoatability may be adversely affected. In addition, emulsifiers based on organic molecules are potential hazardous substances when used in pharmaceutical or cosmetic formulations or in foods.

In 1907, Pickering described for the first time the preparation of emulsions which were stabilized only by addition of various solids, such as basic copper sulfates, basic iron sulfates or other metal salts. These types of emulsions are also referred to as "Pickering emulsions". Basic investigations showed that a characteristic of Pickering emulsions is that solid particles are arranged at the interface between the two liquid phases and form a barrier there to the coalescence of the disperse phase.

In this case, it was shown that although such solid-stabilized emulsions, as were described, for example, in DE 198 42 787, are markedly stable against coalescence of the disperse (oil) phase, they have high viscosities, in particular at phase volumes Φ of the disperse phase of greater than or equal to 0.5, which can have negative effects on the application properties of the emulsions. Attempts at achieving low viscosities by reducing the phase volume of the disperse phase or through lower use amounts of particulate emulsifier often lead to unsatisfactory separation-stable emulsions.

Precise setting of the viscosity according to the requirements of the relevant application is imperative for successful use of emulsions, for example as coating material.

SUMMARY OF THE INVENTION

It was an object of the invention to overcome the disadvantages of the prior art. These and other objects were achieved through adjusting emulsion viscosity through varying the electrolyte concentration of the continuous phase.

DETAILED DESCRIPTION OF THE PREFERRED EMBODIMENTS

The invention relates to emulsions of the oil-in-water (O/W) type, containing:
- an oil phase (phase A), consisting of one substantially water-insoluble component or optionally a plurality of substantially water-insoluble components,
- a water phase (phase B) which may optionally contain further water-soluble components, such as organic compounds, such as alcohols, carboxylic acids or other compounds,
- pyrogenic silica which is arranged at the oil-water interface and is partly silylated in a manner such that the content of non-silylated surface silanol groups on the silica surface is from not more than 95% to not less than 50% of the starting silica, equivalent to from 1.7 to 0.9 SiOH groups per $nm^2$ of silica surface, the dispersion fraction of the surface energy gamma-s-D is from 30 to 80 $mJ/m^2$ and the specific BET surface area has a value of from 30 to 500 $m^2/g$,
- an electrolyte content in the aqueous phase, which is set such that the ionic strength I of the solution is greater than $10^{-6}$ mol/l, where the ionic strength is defined as $I=\frac{1}{2}\cdot\Sigma c_i\cdot z_i^2$, where $c_i$ in this case is the concentration of the ion i in the solution, $z_i$ is the charge of the ion i,
- the mean particle size of the disperse phase, i.e. the mean drop diameter, measured by means of laser diffraction, is from 0.5 µm to 500 µm.
- and optionally further substances, such as pigments or preservatives.

It was surprising and by no means to be foreseen by the person skilled in the art that the rheological properties of the emulsions can be set according to the requirements of the application by using sinter-aggregated pyrogenic silica as a particulate emulsifier and relatively small amounts of electrolyte.

Here, sinter aggregates are secondary structures according to DIN 53206, which are permanent under shear conditions as usually occur on dispersing fillers in liquid media, such as, for example, solvent-containing or solvent-free adhesives or coating materials, i.e. cannot be divided into their primary particles. This can be demonstrated, for example, from TEM images of hardened silica-binder dispersions which have only aggregate structures but no isolated primary particles.

Particulate systems consisting of sinter aggregates are furthermore characterized in that the hydrodynamic equivalent diameter obtained in the particle size determination by means of quasielastic light scattering is at least a factor of 2 greater than the diameter of the primary particles obtainable computationally according to the formula $a=6/A_{BET}\cdot d$, where $A_{BET}$ is the specific BET surface area measured by means of nitrogen adsorption according to DIN 66131 and d is the density of the primary particles.

Sinter-aggregated systems are furthermore characterized in that the fractal dimension df of the mass is preferably less than 2.7, where the fractal dimension df is defined as mass proportional to the radius R to the power df. The fractal dimension of the mass can be determined, for example, by means of small angle X-ray or neutron scattering.

The emulsions according to the invention are preferably substantially free of conventional liquid and solid, purely organic surface-active substances which are not particulate at room temperature and the pressure of the ambient atmosphere, such as nonionic, cationic and anionic emulsifiers.

Here, non-particulate emulsifiers means not particles and colloids but molecules and polymers, following the definition of molecules, polymers, colloids and particles as given in "Dispersionen and Emulsionen [Dispersions and emulsions]", G. Lagaly, O, Schulz, R. Zindel, Steinkopff, Darmstadt 1997, ISBN 3-7985-1087-3, page 14. In general, these organic emulsifiers have a size of less than 1 nm, a molar mass of <10,000 g/mol, a carbon content of >50% by weight, determinable by elemental analysis, and a Mohs' hardness of less than 1.

At the same time, the emulsifiers, of which the emulsions according to the invention are preferably substantially free, generally have a solubility of more than 1% by weight in water at 20° C. and the pressure of the ambient atmosphere, i.e. from 900 to 1100 hPa, in homogeneous or in micellar form. The emulsions according to the invention may contain such surface-active substances up to a maximum concentration of less than 0.1 times, preferably less than 0.01 times, particularly preferably less than 0.001 times, in particular less than 0.0001 times, the critical micelle concentration of these surface-active substances in the water phase; this corresponds to a concentration of these surface-active substances, based on the total weight of the emulsion according to the invention, of less than 10% by weight, preferably less than 2% by weight, more preferably less than 1% by weight, in particular 0% by weight.

The emulsion according to the invention contains an oil phase (phase A). Phase A consists of one substantially water-insoluble component, optionally a plurality of substantially water-insoluble components. Here, substantially water-insoluble means that the solubility of the components in water alone or as a mixture is less than 10 g/100 g of water, preferably less than 1 g/100 g of water, particularly preferably less than 0.1 g/100 g of water, measured at 20° C. and the pressure of the ambient atmosphere, i.e. from 900 to 1100 hPa.

In the emulsion according to the invention, the viscosity of phase A, measured at 20° C. and a shear gradient of $10\ s^{-1}$, is from 0.1 to 1,000,000 mPa·s, preferably from 0.1 to 500,000 mPa·s, more preferably from 0.2 to 100,000 mPa·s.

In the emulsion according to the invention, the phase A can preferably contain a plurality of components. The individual components may be both substances which are liquid at 20° C. and solids, the total mixture of the individual components having the abovementioned viscosity. Preferably, but not necessarily, a multicomponent phase A is a true solution, i.e. a homogeneous phase in which no further phase interfaces occur.

Examples of substantially water-insoluble components as may be formed by the phase A of an emulsion according to the invention or may be present in it are aliphatic and aromatic hydrocarbons, alcohols, aldehydes, ketones, ethers, esters, amines, carboxylic acids and derivatives thereof, mercaptans, thioethers, oligomeric or polymeric compounds, such as polyolefins, such as polystyrenes, polypropylenes or polyethylenes, saturated or unsaturated polyesters, such as, for example, polycondensates of phthalic acids and 1,2-propanediols or polycocondensates of phthalic acids, 1,2-propanediols and maleic acids, optionally dissolved in reactive diluents, such as styrenes, polyethers, polyepoxides or monomeric or oligomeric precursors thereof, such as alkylene bis-glycidyl ethers, such as

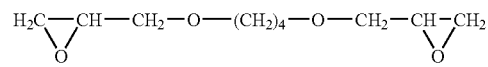

bisphenol A-based diglycidyl ethers, such as

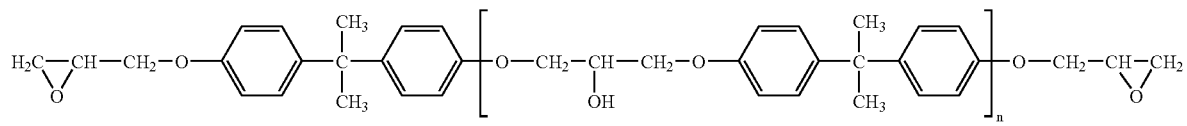

with n preferably from 0 to 10, particularly preferably from 0 to 5.

Examples of epoxy novolac resins are those of the formula

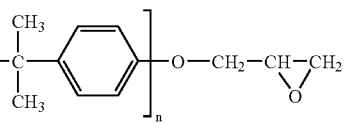

bifunctional epoxy compounds, such as

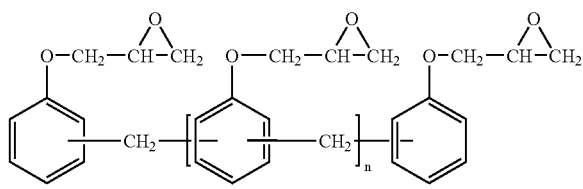

trifunctional epoxy compounds, such as

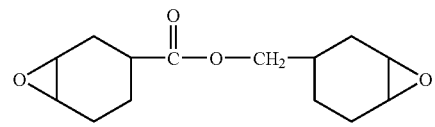 [SMILES: O=C(OCC1CCC2OC2C1)C1CCC2OC2C1]

tetrafunctional epoxy compounds, such as

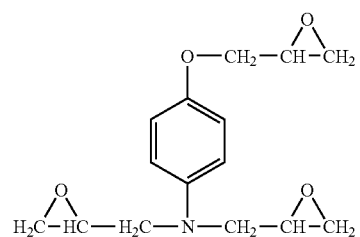 [SMILES: c1cc(N(CC2CO2)CC2CO2)ccc1OCC1CO1]

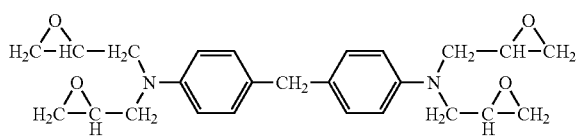

polyurethanes or monomeric or oligomeric precursors thereof, such as, for example, polyetherpolyols, polyacrylatepolyols, polyesterpolyols, polyfunctional isocyanates, such as hexane diisocyanate, toluene diisocyanate, diphenylmethane diisocyanate or isocyanates provided with blocking protective groups, such as hydroxylamines or malonic ester derivatives, complex organic compounds, such as synthetic or natural pharmaceutical or cosmetic active substances, dyes, organo-element compounds, such as organosilicon compounds, such as organo(poly)silanes, organo(poly)siloxanes, organo(poly)silazanes and organo(poly)silcarbanes, or transition metal compounds. Optionally, phase A may contain oil-wettable particles, such as pigments, fillers or rheological additives.

The emulsion according to the invention furthermore contains an aqueous phase (phase B). In addition to water, phase B may contain further components, such as, preferably, acids, bases, water-soluble organic compounds, such as alcohols, carboxylic acids and derivatives thereof, amines or other organic compounds, polymeric or oligomeric compounds, such as polyols or polyamines or polyamidoamines, complex water-soluble organic compounds, such as synthetic or natural pharmaceutical or cosmetic active substances, dyes, organo-element compounds, such as water-soluble organosilicon compounds or water-soluble transition metal compounds. Optionally, phase B may contain water-wettable particles, such as pigments, fillers or rheological additives.

To set the required viscosity of the emulsion, organic or inorganic (poly)electrolytes may furthermore be added to the water phase B in such a manner that the ionic strength in the aqueous phase is preferably less than 160 mol/l, more preferably $10^{-6}$ mol/l to 16 mol/l, particularly yet more preferably $10^{-5}$ mol/l to 1.6 mol/l and most preferably $10^{-4}$ mol/l to 0.8 mol/l, where the ionic strength is defined as $I=\frac{1}{2}\cdot\Sigma c_i\cdot z_i^2$, $c_i$ is in this case the concentration of the ion i in the solution, $z_i$ the charge of the ion i.

The emulsions according to the invention contain sinter aggregates of suitable pyrogenic silicas, which sinter aggregates are arranged at the oil-water interface. The sinter aggregates used according to the invention are sinter aggregates partly wettable with water, i.e. which are not completely wettable with water and not completely water-unwettable.

The sinter aggregates used according to the invention are sinter aggregates which are solid at room temperature and the pressure of the ambient atmosphere, i.e. between 900 and 1100 hPa.

The sinter aggregates used according to the invention preferably have a solubility in water, at pH 7.33 and an electrolyte background of 0.11 mol and a temperature of 37° C., of less than 0.1 g/l, particularly more preferably of less than 0.05 g/l, at the pressure of the ambient atmosphere, i.e. between 900 and 1100 hPa.

Preferably, the sinter aggregates used according to the invention have a mean hydrodynamic equivalent diameter $D_h$ of greater than 1 nm, more preferably from 1 to 5000 nm, yet more preferably from 10 to 1000 nm, and still more preferably from 100 to 600 nm, most preferably from 200 nm to 500 nm, and especially from 210 nm to 450 nm, measured in each case preferably by means of dynamic light scattering.

This means that the collision radius $R_c$ of the sinter aggregates which is relevant for the formation of a particle layer in the oil-water interface is greater than 0.8 nm, preferably from 0.8 to 4000 nm, more preferably from 8 to 850 nm, still more preferably from 80 to 500 nm, and most preferably from 170 nm to 375 nm. The collision radius is the radius of the smallest sphere which just includes all constituents of an aggregate, the collision radius $R_c$ being obtained from the equation $R_c=[R_h^2/0.76+2.63\cdot R_h^2/d_f]^{0.5}$, as stated in R. de Rooij, A. A. Potanin, D. van den Ende, J. Mellema, *J. Chem. Phys.* 1993, 99, 9213, the hydrodynamic equivalent radius $R_h$ being obtained from the hydrodynamic equivalent diameter divided by 2 and the fractal dimension of the mass $d_f$ having a value of 1.8.

The sinter aggregates used according to the invention are furthermore preferably characterized in that, in the particle size determination by means of quasielastic light scattering, the hydrodynamic equivalent diameter is at least a factor of 2, preferably a factor of from 5 to 50, more preferably a factor of from 7 to 25, and most preferably a factor of from 7.5 to 16.5, based in each case on a specific surface area of 100 m²/g (the factor decreases or increases in a correspondingly linear manner in the case of a smaller or larger surface area), greater than the primary particle diameter obtainable computationally according to the formula $a=6/A_{BET}\cdot d$, $A_{BET}$ being the specific BET surface area measured by means of nitrogen adsorption according to DIN 66131 and d being the density of the primary particles.

The sinter aggregates used according to the invention preferably have a molar mass greater than 10,000 g/mol, more preferably a molar mass of from 50,000 to 50,000,000 g/mol, in particular and most preferably from 10,000,000 g/mol, measured in each case preferably by means of static light scattering.

The sinter aggregates used according to the invention preferably have a specific BET surface area of from 30 to 500 m²/g, more preferably from 80 to 300 m²/g. The BET surface area is measured by known methods, preferably according to German Industrial Standard DIN 66131 and DIN 66132.

The sinter aggregates used according to the invention preferably have a carbon content of less than 50 percent by weight. a Mohs' hardness greater than 1. more preferably greater than 4, and a surface energy gamma of from 30 to 72.5 mJ/m² at a temperature of 25° C. and the pressure of the ambient atmosphere, i.e. between 900 and 1100 hPa.

The silica sinter aggregates used according to the invention preferably have a dispersion fraction of the surface energy gamma-s-D of from 30 to 80 mJ/m², more preferably from 35 to 70 mJ/m², most preferably from 40 to 70 mJ/m², at a temperature of 25° C. and the pressure of the ambient atmosphere, i.e. between 900 and 1100 hPa. The dispersion fraction of the surface energy gamma-s-D is measured, for example, according to "Inverse Gas Chromatography"—" Characterisation of Polymers and other Materials", 391 ACS Symposium Series, D R Lloyd, Th C Ward, H P Schreiber, Chapter 18, pages 248-261, ACS, Washington D.C., 1989, ISBN 0-8412-1610-X.

The preferred starting silica, from which the silica used in the emulsions according to the invention and partly wettable with water can be prepared, can be prepared in any desired manner known per se, such as, for example, in a flame reaction from halogen-silicon compounds, for example from silicon tetrachloride, or halogen-organosilicon compounds, such as methylchlorosilanes, such as methyltrichlorosilane, or hydrogenchlorosilanes, such as hydrogentrichlorosilane, or other hydrogenmethylchlorosilanes, such as hydrogenmethyldichlorosilane, or alkylchlorosilanes, also as a mixture with hydrocarbons, or any desired sprayable and, preferably, volatilizable mixtures of organosilicon compounds, as mentioned, and hydrocarbons, it being possible for the flame to be a hydrogen-oxygen flame or a carbon monoxide-oxygen flame. The preparation of the silica can be effected alternatively with or without further addition of water, for example in the purification step; preferably, no water is added.

Preferably, partly hydrophobized, more preferably partly silylated, silica sinter aggregates are used as silica sinter aggregates for the preparation of the emulsions according to the invention.

Here, partly silylated means that neither is the total silica surface unsilylated nor is the total silica surface silylated.

The degree of coverage τ of the surface of the silica sinter aggregates with silylating agent radicals is preferably from 5 to 95%, more preferably from 10 to 90%, in particular from 15% to 75%, based on the total particle surface.

The coverage with silylating agent can be determined, for example, by means of elemental analysis, such as, for example, via the carbon content, or by determination of the residual content of reactive surface silanol groups of the silica sinter aggregates.

Partial silylation means in this case that the carbon content of silica is from 0.1 to 10% by weight, preferably from 0.1 to 5% by weight, more preferably from 0.1 to 3% by weight, and in particular from 0.1 to 1.5% by weight.

Partial silylation furthermore means that the content of non-silylated surface silanol groups on the silica surface is from not more than 95% to not less than 50%, more preferably from 90 to 60%, in particular from 85 to 65%, of the starting silica.

This means that the density of the surface silanol groups SiOH is preferably from not less than 0.9 to not more than 1.7, more preferably from 1.1 to 1.6, most preferably from 1.2 to 1.55, SiOH per nm² of particle surface.

For a starting silica of 200 m²/g of specific surface area, which can be used for the silylation, this preferably means not less than 0.3 mmol/g of SiOH and not more than 0.57 mmol/g of SiOH, more preferably from 0.36 to 0.54 mmol/g of SiOH, most preferably from 0.39 to 0.51 mmol/g of SiOH; for a silica having a smaller or large surface area, this means linearly proportionally more or less surface silanol groups SiOH.

Processes for the partial hydrophobing or partial silylation of solid particles are already known.

Preferably, the starting silica has a specific BET surface area of from 25 to 500 m²/g. The starting silica preferably has sinter aggregates (definition according to DIN 53206) in the range of diameters from 200 to 1000 nm, the silica having agglomerates (definition according to DIN 53206) which are composed of sinter aggregates and, depending on the external shear load (e.g. measuring conditions), have sizes of from 1 to 500 μm.

The starting silica preferably has a fractal dimension of the surface of preferably less than or equal to 2.3, the fractal dimension of the surface $D_s$ being defined here as: particle surface A is proportional to the particle radius R to the power of $D_s$. Preferably, the starting silica has a density of accessible surface silanol groups SiOH, i.e. accessible to a chemical reaction, of preferably from 1.5 to 2.5 SiOH per nm² of specific surface area, more preferably from 1.6 to 2.0 SiOH per nm².

For the preparation of the silica sinter aggregates used according to the invention, silicas prepared at high temperature (greater than 1000° C.) can be used as starting silicas, pyrogenically prepared silicas being particularly preferred. It is possible to use hydrophilic silicas which are freshly prepared and obtained directly from the burner, have been temporarily stored or are already in commercial packaging.

Uncompacted silicas having tamped or tapped densities of less than 60 g/l, but also compacted silicas having tamped or tapped densities greater than 60 g/l can be used as starting silicas.

Mixtures of different silicas can be used as starting silicas, for example mixtures of silicas of different BET surface area.

For the silylation of silicas, organosilicon compounds, such as, for example, (i) organosilanes or organosilazanes of the formula

$$R^1_d SiY_{4-d} \qquad (I)$$

and/or partial hydrolysis products thereof, where

R¹ may be identical or different and is a monovalent, optionally substituted, optionally mono- or polyunsaturated, optionally aromatic hydrocarbon radical having 1 to 24 carbon atoms which may be interrupted by oxygen atoms, d is 1, 2 or 3 and Y may be identical or different and is a halogen atom, monovalent Si—N-bonded nitrogen radical to which a further silyl radical may be bonded, —OR², or —OC(O)OR², where R² is a hydrogen atom or a monovalent, optionally substituted, optionally mono- or polyunsaturated hydrocarbon radical which may be interrupted by oxygen atoms, or (ii) linear, branched or cyclic organosiloxanes comprising units of the formula

$$R^3_e(OR^4)_f SiO_{(4-e-f)/2} \qquad (II)$$

where

R³ may be identical or different and has one of the meanings stated above for R¹, R⁴ may be identical or different and has a meaning stated for R³, e is 0, 1, 2 or 3 and f is 0, 1, 2 or 3, with the proviso that the sum e+f is ≤3, or mixtures of (i) and (ii)

can preferably be used.

The organosilicon compounds which may be used for the silylation of the silicas may be, for example, mixtures of silanes or silazanes of the formula (I), those comprising methylchlorosilanes on the one hand or alkoxysilanes and optionally disilazanes on the other hand being preferred.

Examples of R¹ are the abovementioned radicals, preference being given to the methyl, octyl, phenyl and vinyl radical, particularly preferably the methyl radical.

Examples of R² are preferably the methyl, the ethyl, the propyl and the octyl radical, the methyl and the ethyl radical being preferred.

Examples of organosilanes of the formula (I) are alkylchlorosilanes, such as methyltrichlorosilane, dimethyldichlorosilane, trimethylchlorosilane, octylmethyldichlorosilane, octyltrichlorosilane, octadecylmethyldichlorosilane and octadecyltrichlorosilane, methylmethoxysilanes, such as methyltrimethoxysilane, dimethyldimethoxysilane and trimethylmethoxysilane, methylethoxysilanes, such as methyltriethoxysilane, dimethyldiethoxysilane and trimethylethoxysilane, methylacetoxysilanes, such as methyltriacetoxysilane, dimethyldiacetoxysilane and trimethylacetoxysilane, phenylsilanes, such as phenyltrichlorosilane, phenylmethyldichlorosilane, phenyldimethylchlorosilane, phenyltrimethoxysilane, phenylmethyldimethoxysilane, phenyldimethylmethoxysilane, phenyltriethoxysialne, phenylmethyldiethoxysilane and phenyldimethylethoxysilane, vinylsilanes, such as vinyltrichlorosilane, vinylmethyldichlorosilane, vinyldimethylchlorosilane, vinyltrimethoxysilane, vinylmethyldimethoxysilane, vinyldimethylmethoxysilane, vinyltriethoxysilane, vinylmethyldiethoxysilane and vinyldimethylethoxysilane, disilazanes, such as hexamethyldisilazane, divinyltetramethyldisilazane and bis(3,3-trifluoropropyl)tetramethyldisilazane, cyclosilazanes, such as octamethylcyclotetrasilazane, and silanols, such as trimethylsilanol.

Methyltrichlorosilane, dimethyldichlorosilane and trimethylchlorosilane or hexamethyldisilazane are preferred.

Examples of organosiloxanes of the formula (II) are linear or cyclic dialkylsiloxanes having an average number of dialkylsilyloxy units of more than 3. The dialkylsiloxanes are preferably dimethylsiloxanes. Particularly preferred are linear polydimethylsiloxanes having the following terminal groups: trimethylsilyloxy, dimethylhydroxysilyloxy, dimethylchlorosilyloxy, methyldichlorosilyloxy, dimethylmethoxysilyloxy, methyldimethoxysilyloxy, dimethylethoxysilyloxy, methyldiethoxysilyloxy, dimethylacetoxysilyloxy, methyldiacetoxysilyloxy and dimethylhydroxysilyloxy groups, in particular having trimethylsilyloxy or dimethylhydroxysilyloxy terminal groups.

Said polydimethylsiloxanes preferably have a viscosity at 25° C. of from 2 to 100 mPa·s.

Further examples of organosiloxanes are silicone resins, in particular those which contain methyl groups as alkyl groups, more preferably those which contain $R^3_3SiO_{1/2}$ and $SiO_{4/2}$ units or those which contain $R^3SiO_{3/2}$ and optionally $R^3_2SiO_{2/2}$ units, $R^3$ having one of the abovementioned meanings.

Said silicone resins comprising units of the formula (II) preferably have a viscosity at 25° C. of from 500 to 5000 $mm^2/s$.

Preferred silicone resins having a viscosity greater than 1000 $mm^2/s$ at 25° C. are those which can be dissolved in a solvent which can be easily handled technically, such as, preferably alcohols such as methanol, ethanol, isopropanol, ethers, such as diethyl ether, tetrahydrofuran, siloxanes, such as hexamethyldisiloxane, alkanes, such as cyclohexane or n-octane, aromatics, such as toluene or xylene, in a concentration above 10% by weight and with a viscosity of the mixture of less than 1000 $mm^2/s$ at a temperature of 25° C. and the pressure of the ambient atmosphere.

Preferred among the solid organosiloxanes are those which dissolve in a solvent which can be easily handled technically (as defined above) in a concentration greater than 10% by weight and with a viscosity of the mixture of less than 1000 $mm^2/s$ at a temperature of 25° C.

The hydrophobing and silylation, which is preferably carried out for the preparation of the silica sinter aggregates used according to the invention, can be carried out as a batchwise reaction, i.e. by the batch process, or as a continuous reaction, the continuous reaction being preferred.

The hydrophobing and silylation can be realized in one step or in 2 or 3 successive steps. This means that loading (physisorption of the silylating agent) can be effected upstream of the reaction and preferably a purification step can be effected downstream of the reaction. 3 successive steps are preferred: (1) loading—(2) reaction—(3) purification.

The loading temperature is preferably from −30 to 350° C., preferably from 20 to 120° C.

The reaction temperatures preferably range from 0 to 400° C., particularly preferably from 20 to 330° C.

The reaction times are preferably from 1 minute to 24 hours, preferably from 30 minutes to 4 hours.

The reaction pressure is preferably in the region of atmospheric pressure, i.e. between 900 and 1100 hPa.

The purification temperature preferably ranges from 80 to 400° C.

Effective movement and thorough mixing of silica and silylating agent are necessary during steps (1) loading, (2) reaction and purification (3). This is preferably effected by mechanical or gas-borne fluidization. Gas-borne fluidization can be effected by all inert gases which do not lead to secondary reactions, degradation reactions, oxidation processes and flame and explosion phenomena. Here, the superficial gas velocity is from 0.05 to 5 cm/s, particularly preferably from 0.05 to 1 cm/s. Mechanical fluidization can be effected by means of paddle stirrers, anchor stirrers and other suitable stirring members.

In a particularly preferred embodiment, only the amount of gas which is sufficient for maintaining an atmosphere with a low oxygen content, preferably less than 5% by volume, is fed in, and the fluidization is then effected purely mechanically.

The reaction is preferably carried out in an atmosphere which does not lead to oxidation of the silylated silica, i.e. preferably less than 10% by volume of oxygen, more preferably less than 2.5% by volume, best results being obtained at less than 1% by volume of oxygen.

Effective introduction of the silylating agent into the silica takes place. If the silylating agents are liquid compounds at the application temperature, effective spraying techniques are preferably used. Spraying in unary nozzles under pressure (from 5 to 20 bar), spraying in binary nozzles under pressure (gas and liquid, from 2 to 20 bar), very fine distribution using atomizers, etc.

The silylating agent is preferably added as a very finely divided aerosol, the aerosol having a settling rate of, preferably, from 0.1 to 20 cm/s and a drop size with an aerodynamic equivalent diameter of from 5 to 25 μm.

Alternatively, protic solvents can preferably be added, such as liquid or vaporizable alcohols or water; typical alcohols are isopropanol, ethanol and methanol. It is also possible to add mixtures of the abovementioned protic solvents. Preferably, no protic solvents are added.

Alternatively, acidic or basic catalysts can preferably be added. These catalysts may have a basic character in the sense of a Lewis base or a Brønsted base, such as ammonia, or acidic character, in the sense of a Lewis acid or a Brønsted acid, such as hydrogen chloride. If catalysts are used, traces are preferred, i.e. less than 1000 ppm. Most preferably, no catalysts are added.

The purification step is characterized by movement, slow movement and slight mixing being preferred.

The purification step is furthermore characterized by increased introduction of gas, corresponding to a superficial gas velocity of from 0.001 to 10 cm/s.

In addition, the purification step may comprise mixing by means of mechanical stirring members. The stirring members are adjusted and moved so that preferably mixing and fluidization but not complete vortexing occur.

In addition, methods from mechanical compaction, such as, for example, press rolls, ball mills, edge mills, screw compactors and briquetters, can be used during the silylation step.

In addition, processes for the deagglomeration of the silica, such as pin-disk mills or apparatuses for milling classification, and/or methods for mechanical compaction of the silica, such as, for example, press rolls, or compaction by sucking out the air or gas content by suitable vacuum methods, or other methods for mechanical compaction, such as, for example, press rolls, ball mills, edge mills, screw compactors and briquetters, can be used before, during or after the silylation step.

The preparation of the silica sinter aggregates can also be effected in situ in the preparation of the emulsions according to the invention.

The emulsions according to the invention contain silica sinter aggregates in amounts of, preferably, from 0.1 to 50 parts by weight, more preferably from 1 to 15 parts by weight, in particular from 2 to 10 parts by weight, based on 100 parts by weight of total emulsion.

In the case of the emulsions according to the invention, the volume fraction $\Phi_w$ of the oil phase, defined as $\Phi_w$=volume of oil phase/(volume of oil phase+volume of water phase), can preferably be from 0.1 to 0.9, preferably from 0.2 to 0.8, more preferably from 0.3 to 0.75, in particular from 0.4 to 0.7.

In the case of the emulsions according to the invention, the volume fraction $\Phi_w$ of the water phase, defined as $\Phi_w$=volume of water phase/(volume of oil phase+volume of water phase), can preferably be from 0.1 to 0.9, preferably from 0.2 to 0.8, more preferably from 0.25 to 0.7, in particular from 0.3 to 0.6.

The emulsions according to the invention are characterized in particular in that they contain inorganic or organic electrolytes for establishing the flow properties. The addition of electrolytes leads to an increase in the viscosity. Preferably, more than $10^{-6}$ mol/l of electrolyte, more preferably from $10^{-6}$ mol/l to 1 mol/l of electrolyte, yet more preferably from $10^{-5}$ mol/l to 0.1 mol/l of electrolyte and most preferably from $10^{-4}$ mol/l to 0.05 mol/l of electrolyte is added to the emulsion. The addition of the electrolyte can be effected during the emulsification process or subsequently for establishing the viscosity.

The emulsions according to the invention are furthermore characterized in that the ionic strength I of the emulsion is more than $10^{-6}$ mol/l, more preferably from $10^{-6}$ mol/l to 16 mol/l, yet more preferably from $10^{-5}$ mol/l to 1.6 mol/l and most preferably from $10^{-4}$ mol/l to 0.8 mol/l, the ionic strength I being defined as $I=\frac{1}{2}\cdot\Sigma c_i\cdot z_i^2$, where $c_i$ is the concentration of the $i^{th}$ ion and $z_i$ is the charge thereof.

The electrolyte can be added during the preparation of the emulsion or subsequently to the prepared emulsion. Subsequent addition is preferred.

The electrolytes may be low molecular weight organic or inorganic compounds or high molecular weight oligoelectrolytes or polyelectrolytes.

The electrolytes used according to the invention can be employed in the form of a pure substance or as a mixture of different electrolytes. Pure substances are preferred.

Examples of electrolytes which can be used according to the invention are soluble halides, nitrates, nitrites, sulfates, sulfites, phosphates, phosphites of metals or semimetals of the 1st to 4th main group, such as lithium chloride, sodium chloride, potassium chloride, lithium bromide, sodium bromide, potassium bromide, lithium sulfate, sodium sulfate, potassium sulfate, lithium nitrate, sodium nitrate, potassium nitrate, lithium phosphate, sodium phosphate, potassium phosphate, magnesium chloride, calcium chloride, barium chloride, magnesium sulfate, magnesium nitrate, calcium nitrate, barium nitrate, magnesium phosphate, aluminum chloride, aluminum nitrate, aluminum sulfate, lead nitrate, lead chloride; soluble halides, nitrates, nitrites, sulfates, sulfites, phosphates, phosphites of metals of the 1st to 10th subgroup, such as titanium tetrachloride, chromium trichloride, iron dichloride, iron trichloride, nickel chloride, zinc chloride, zirconium tetrachloride, zinc sulfate, zinc nitrate, iron sulfate.

Examples of further electrolytes which may be used are the alkali metal and alkaline earth metal salts of organic acids, such as sodium formate, sodium acetate, sodium citrate, sodium tartrate, sodium methacrylate, potassium formate, potassium acetate, potassium citrate, potassium tartrate, potassium methacrylate.

Further examples are water-soluble tetraalkylammonium compounds, such as tetramethylammonium chloride, tetraethylammonium chloride, tetramethylammonium bromide, and tetraethylammonium bromide.

Examples of polyelectrolytes are polytetraalkylammonium compounds, such as polydiallyldimethylammonium chloride, polymethacrylates or polyacrylates.

Preferred electrolytes are alkali metal and alkaline earth metal salts, and sodium and calcium salts are particularly preferred, sodium chloride and calcium chloride being very particularly preferred.

The emulsions according to the invention are characterized in particular in that, by adding the electrolytes mentioned above by way of example, the viscosity of the emulsion increases and the relative viscosity $\eta_{rel}$ has a value greater than 1.005. Preferably, $\eta_{rel}>1.005$ at an ionic strength I of the emulsion according to the invention in the range from $1\cdot10^{-5}$ mol/l to 200 mol/l; $\eta_{rel}$ is preferably >1.005 at an ionic strength I of the emulsion according to the invention in the range from $5\cdot10^{-5}$ mol/l to 100 mol/l and $\eta_{rel}$ is very particularly preferably >1.005 at an ionic strength I of the emulsion according to the invention in the range from $1\cdot10^{-4}$ mol/l to 20 mol/l, the relative viscosity $\eta_{rel}$ being defined as $\eta_{rel}=\eta/\eta_0$, where $\eta$ is the absolute viscosity of the emulsion according to the invention and $\eta_0$ is the absolute viscosity of the starting emulsion at an ionic strength of $I\leq1\cdot10^{-6}$ mol/l, measured in each case at a shear rate of 10 s$^{-1}$ and a temperature of 25° C. using a cone-and-plate measuring system and a measuring gap of 105 μm.

The emulsions according to the invention are furthermore characterized in that they have a viscosity greater than 0.001 Pas at a conductivity of the emulsion which is greater than or equal to 1 μS·cm$^{-1}$. The viscosity is preferably from 0.05 Pas to $1\cdot10^6$ Pas, at a conductivity of the emulsion in the range from from 1 μS·cm$^{-1}$ to 10 S·cm$^{-1}$, the viscosity is preferably from 0.1 Pas to $5\cdot10^5$ Pas at a conductivity of the emulsion in the range from 1 μS·cm$^{-1}$ to 10 S·cm$^{-1}$, the viscosity is very particularly preferably from 0.1 Pas to $1\cdot10^5$ Pas at a conductivity of the emulsion in the range from 1 μS·cm$^{-1}$ to 5 S·cm$^{-1}$ and, in a special embodiment, the viscosity is from 0.1 Pas to $1\cdot10^5$ Pas at a conductivity of the emulsion in the range from 1 μS·cm$^{-1}$ to 0.1 S·cm$^{-1}$, the viscosity being measured at a shear rate of 10 s$^{-1}$ and a temperature of 25° C. using a cone-and-plate measuring system and a measuring gap of 105 μm and the conductivity of the emulsion being obtained according to conductivity of the emulsion=measured conductivity/volume fraction of the water phase, and the conductivity of the emulsion is measured by means of a conductivity measuring cell QCond 2400.

The emulsions are furthermore characterized in that, when electrolyte is added according to the invention, the loss factor tan δ has a value of less than 1. Preferably, tan δ is <1 at an ionic strength I in the range from $1\cdot10^{-5}$ mol/l to 200 mol/l, tan δ is preferably <1 at an ionic strength I in the range from $5\cdot10^{-5}$ mol/l to 100 mol/l and tan δ is very particularly preferably <1 at an ionic strength I in the range from $1\cdot10^{-4}$ mol/l to 20 mol/l, where tan δ is defined as the quotient G"/G' of the loss modulus G" and of the storage modulus G', and tan δ was obtained as an initial plateau value in the linear viscoelastic range, determined by an oscillation experiment with variation of the shear stress amplitude from 0.05 Pa to 10 Pa at a constant angular velocity ω=6.28 rad/s using a cone-and-plate sensor system with a measuring gap of 105 μm at a temperature of 25° C. and a volume fraction $\Phi_w$ of the water phase of 0.5.

This furthermore means that the emulsions according to the invention have a loss factor tan δ of less than 1 at a conductivity of the emulsion which is greater than or equal to 1 μS·cm$^{-1}$. tan δ is preferably <1 at a conductivity of the emulsion in the range from 5 μS·cm$^{-1}$ to 10 S·cm$^{-1}$, and tan δ is particularly preferably <1 at a conductivity of the emulsion in the range from 10 μS·cm$^{-1}$ to 0.1 S·cm$^{-1}$, where tan δ is defined as the quotient G"/G' of the loss modulus G" and of the storage modulus G', and tan δ was obtained as an initial plateau value in the linear viscoelastic range, determined by an oscillation experiment with variation of the shear stress amplitude from 0.05 Pa to 10 Pa at a constant angular velocity ω=6.28 rad/s using a cone-and-plate sensor system with a measuring gap of 105 μm at a temperature of 25° C. and a volume fraction $\Phi_w$ of the water phase of 0.5, and the conductivity of the emulsion is obtained according to conductivity of the emulsion=measured conductivity/volume fraction of the oil phase, and the conductivity of the emulsion is measured by means of a conductivity measuring cell QCond 2400.

The emulsions according to the invention are further characterized in that the mean particle size of the disperse phase, i.e. the mean drop diameter, measured by means of laser diffraction, for example on a laser diffraction apparatus from Sympatec by the cell measuring technique, is preferably from 0.5 μm to 500 μm, preferably from 0.7 μm to 100 μm, particularly preferably from 0.7 μm to 50 μm and very particularly preferably from 0.7 μm to 20 μm.

A further subject is a process for the preparation of the emulsions, a highly concentrated finely divided dispersion of the corresponding silica in the liquid which forms the homogenous phase in the emulsion being prepared in a first step, and a highly viscous preemulsion which comprises the total amount of the disperse phase and the highly concentrated finely divided dispersion of the silica, prepared in the first step, in the liquid which forms the homogeneous phase in the emulsion according to the invention being prepared in a second step, the volume of dispersion used being such that the total amount of sinter-aggregated silica required is present, and the remaining homogeneous phase being slowly metered in in a third step and an electrolyte being metered in in any one of the steps.

An emulsification process in which a state of high viscosity, referred to below as "stiff phase", is passed through during emulsification proved to be important for achieving the above-described properties of the emulsions according to the invention.

Specifically, the process for the preparation of the emulsions according to the invention comprises the following individual steps:
Preparation of a highly concentrated finely divided dispersion of the corresponding suitable silica in the liquid which forms the homogeneous phase in the emulsion according to the invention.
Preparation of highly viscous preemulsion consisting of the highly concentrated finely divided dispersion of the corresponding suitable silica in the liquid which forms the homogeneous phase in the emulsion according to the invention, the volume used being such that the total amount of the required sinter-aggregated silica is present, and the total amount of the dispersed phase
slow metering in of the remaining homogeneous phase with shearing.

The preparation of the highly concentrated finely disperse dispersion of the corresponding suitable silica in the liquid which forms the homogeneous phase in the emulsion according to the invention can in principle be effected according to the known processes for the preparation of silica dispersions, such as incorporation by means of stirring members with high shear effect, such as high-speed stirrers, high-speed dissolvers, rotor-stator systems, ultrasonic dispersers or ball or bead mills.

The concentration of the silica sinter aggregates in the dispersion is between 1 and 80% by weight, preferably between 10 and 60% by weight, more preferably between 10 and 40% by weight and most preferably between 12 and 30% by weight.

The preparation of the highly viscous preemulsion can be effected in principle according to the known processes for the preparation of emulsions, but it has been found that the processes described below are particularly suitable for obtaining the emulsions according to the invention.

Process 1:
Initially introducing the highly concentrated silica dispersion described above, the initially introduced volume being such that it contains the total amount of silica sinter aggregates required.
Slowly metering in the total volume of disperse phase with continuous homogenization, for example by means of a high-speed stirrer, high-speed dissolver or a rotor-stator system.
Then slowly metering in the desired remaining volume of pure homogeneous phase, optionally with continuous homogenization, for example by means of a high-speed stirrer, high-speed dissolver or a rotor-stator system.

Process 2:
Initially introducing the total volume of disperse phase.
Slowly metering in the highly concentrated silica dispersion described above with continuous homogenization, for example by means of a high-speed stirrer, high-speed dissolver or a rotor-stator system, the volume metered in being such that it contains the total amount of silica sinter aggregates required.
Then slowly metering in the desired remaining volume of pure homogeneous phase, optionally with continuous homogenization, for example by means of a high-speed stirrer, high-speed dissolver or a rotor-stator system.

The processes described can be carried out both in continuous and in batchwise form. The continuous form is preferred.

The temperature of the liquid phase during the emulsification process is between 0° C. and 80° C., preferably between 10° C. and 50° C., more preferably between 20° C. and 40° C.

The emulsification process can be carried out at atmospheric pressure, i.e. at from 900 to 1100 hPa, at elevated pressure or in vacuo. The process at atmospheric pressure is preferred.

The emulsions according to the invention can be used for all purposes for which emulsions are already used to date. These are in particular water-based coating materials, adhesives and sealants, containing, for example, organosilicon compounds, such as organo(poly)silanes, organo(poly)siloxanes, organo(poly)silazanes and organo(poly)silcarbanes; polyolefins, such as silyl-terminated polyisobutylenes (for example, obtainable under the brand Epion from Kaneka Corp., Japan); polyurethanes, polyols, such as hydroxyl-containing polyesters, hydroxyl-containing polyethers, methyldimethoxysilylpropyl-terminated polypropylene glycols (for example, obtainable as "MS polymers" from Kaneka Corp., Japan), hydroxyl-containing polyacrylates; polyisocyanates, such as aliphatic and aromatic polyisocyanates, isocyanate-terminated polyurethane prepolymers, prepared by reacting polyols with polyisocyanates in excess, and the silyl-terminated derivatives thereof (for example, obtainable under the name DESMOSEAL® from Bayer AG, Germany); (poly) epoxy compounds, such as bisphenol A-based epoxides, monomeric, oligomeric and polymeric compounds containing glycidyloxy functions, such as diglycidyl ethers based on bisphenol A, epoxy novolac raw materials and resins, epoxyalkyd resins, epoxyacrylates, aliphatic epoxides, such as linear alkylene bisglycidyl ethers, and cycloaliphatic glycidyl ethers, such as 3,4-epoxycyclohexyl 3,4-epoxycyclohexanecarboxylates, and aromatic epoxides, such as triglycidyl ethers of p-aminophenol and triglycidyl ethers of methylenedianiline; (poly)amines, such as cyclic and linear amines, such as hexamethylenediamine, aromatic amines, such as 4,4'-methylenebis(2,6-diethylaniline), bis(2-aminoalkyl) polyalkylene oxide, such as bis(2-aminopropyl)polypropylene glycol, and Jeffamines, (poly)amidoamines, (poly)mercaptans, (poly)carboxylic acid, (poly)carboxylic anhydrides; acrylates and esters thereof, such as glycidyl acrylates, alkyl acrylates and esters thereof, methacrylates and esters thereof, polysulfide-forming polymers and polysulfides, such as thioplasts (for example, obtainable under the brand Thiokol from Toray Thiokol Co. Ltd.).

Examples of epoxy compounds are alkylene bisglycidyl ethers, such as

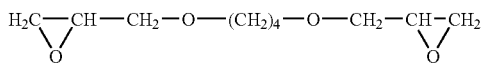

bisphenol A-based diglycidyl ethers, such as

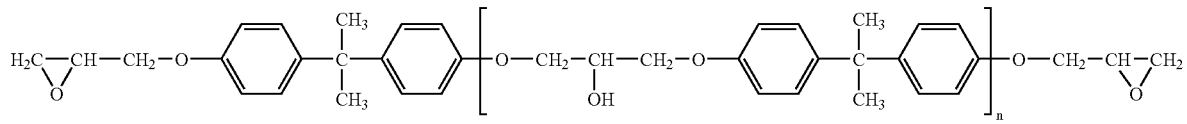

with n preferably from 0 to 10, particularly preferably from 0 to 5.

Examples of epoxy novolac resins are those of the formula

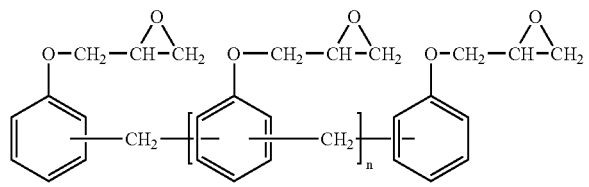

bifunctional epoxy compounds, such as

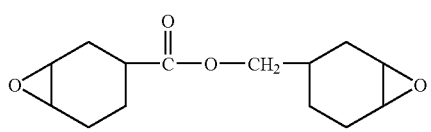 [SMILES: O=C(OCC1CCC2OC2C1)C1CCC2OC2C1]

and trifunctional epoxy compounds, such as

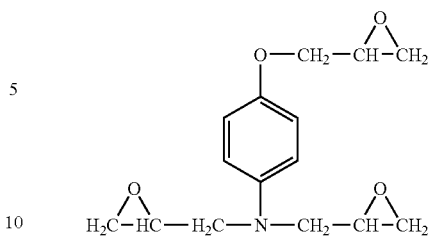

tetrafunctional epoxy compounds, such as

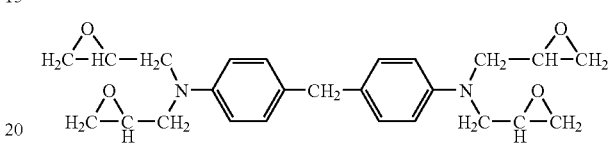

Furthermore, the emulsions according to the invention can be used for cosmetic and pharmaceutical applications, cleaning and cleansing agents or applications for changing the interfacial properties of solid and liquid substrates, such as, for example, water repellents, adhesion promoters, release agents, paper coatings or foam control agents. Furthermore, the emulsions according to the invention can be used for the preparation of w/o/w or o/w/o multiple emulsions, for example as control release systems or for the segregation of reactive substances.

Example 1

Preparation of Solid Particles 100 g of a pyrogenic silica having a specific BET surface area, according to DIN 66131 and DIN 66132, of 200 m²/g (obtainable from Wacker-Chemie GmbH, Munich, Germany, under the name Wacker HDK® N20) are fluidized with stirring (at 1000 rpm with a stirring blade diameter of 12.5 cm) and then treated and blanketed for 15 minutes with nitrogen gas, and the nitrogen stream is then switched off again. Thereafter, 2 g of dimethyldichlorosilane are sprayed by means of a binary nozzle as an aerosol into the fluidized silica, at a temperature of about 25° C. and an ambient pressure of about 1013 hPa. After stirring for a further 30 minutes, the silica thus treated is then heated for 2 hours at 300° C. in an oven having a capacity of 100 l, under a gentle stream of 1000 l/h of nitrogen.

A white pulverulent silica having the following properties is obtained:

The silica has limited but not complete wettability with water; this is evident from the fact that only 18% by weight of the silica can be incorporated into water using Ultraturrax to give a flowable material stable for one day; however, 24% by weight of the starting silica (Wacker HDK® N20), which is completely wettable with water, can be incorporated under the same conditions and at the same viscosity.

Further properties of the silica are summarized in Table 1

TABLE 1

| Property | Silica B1 according to Example 1 |
|---|---|
| BET surface area | 184 m²/g |
| Residual content of non-silylated silica silanol groups | 80% |
| Carbon content % C | 0.5% by weight |
| Methanol number | 0 |
| Contact angle THETA Method 1 against water and air | 84° |
| Contact angle THETA Method 2 against water and air | of 80° |
| Surface energy GAMMA | 69 mJ/m² |
| Dispersion fraction of surface energy GAMMA-s-D | 65 mJ/m² |

Specific BET surface area, measured according to DIN 66131 and DIN 66132

Residual content of non-silylated silica silanol groups, obtained as quotient (a) of the amount of silica silanol group of the silica prepared as mentioned above, divided by the amount of silica silanol groups of the untreated starting silica (Wacker HDK® N20); the amount of silica silanol groups is determined by acid-base titration (analogous to G. W. Sears, Anal. Chem. 28 (12), (1950), 1981). Method: acid-base titration of the silica suspended in water/methanol=50:50; titration in the range above the pH range of the isoelectric point and below the pH range of the dissolution of the silica; untreated silica comprising 100% of SiOH (silica surface silanol groups): SiOH-phil=1.8 SiOH/nm²; silylated silica: SiOH-silyl; residual content of nonsilylated silica silanol groups; % SiOH=SiOH-silyl/SiOH-phil·100% carbon content % C determined by means of elemental analysis for carbon; combustion of the sample at above 1000° C. in an $O_2$ stream, detection and quantification of the resulting $CO_2$ using IR; LECO 244 apparatus Methanol number, measured as follows: test (% by volume of MeOH in water) of the wettability with water-methanol mixtures=methanol number (MN): shaking of an equal volume of silica with an equal volume of water-methanol mixture; start with 0% of methanol; if no wetting occurs, silica floats; a mixture with a 5% by volume higher MeOH content should be used; on wetting, silica sinks: portion of MeOH (%) in water gives the methanol number (MN)

Contact angle THETA method 1 against water, measured as follows: the contact angle of the particles is obtained by careful preparation, by conventional methods, of a pellet of the silica and subsequent determination of the contact angle against water, in this case a deposited water drop comprising bidistilled water in air, by digital image evaluation.

The contact angle θ defines the ratio of the surface tensions and surface energies γ of liquids (1) and solids (s) in a gas space (g) as follows:

$\cos\theta = (\gamma(sl) - \gamma(sg))/\gamma(lg)$

The surface energy (mJ/m²) of a solid is dimensionally identical to the surface tension of a liquid (mN/m), since [J]=[N·m].

Contact angle THETA method 2 against water, measured as by means of an imbibition method using the Lucas-Washburn equation, based on the aspiration of a known and defined liquid, with a known surface tension, into a defined heap, in this case a slightly compacted pellet of the silica having an open porosity greater than 0.25 and a pore radius r. The aspiration rate dh/dt and the height of the aspirated liquid column h are calculated from the mass absorption m of liquid by the particle heap as a function of the time t, and the viscosity of the aspirated liquid η and the surface tension γ of the aspirated liquid make it possible, in the case of a known particle radius r, to calculate the cosine value of θ (cos (θ)) and hence the contact angle θ of the liquid against the particle surface by means of the equation according to Lucas-Washburn (Washburn, E. W., Phys. Rev. 17, 273 (1921) and R. Lucas, Kolloid s. 23, 15 (1918)); following J. Schoelkopf et al., J. Colloid. Interf. Sci. 227, 119-131 (2000).

Methanol-water mixtures having mixing ratios (volume of methanol to volume of water) are 0:100, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, 100:0 are used as liquid having a known surface tension.

$dh/dt = r \cdot \gamma \cdot \cos(\theta)/(4 \cdot \eta)$ and $h^2 = r \cdot \gamma \cdot t \cdot \cos(\theta)/(2 \cdot \eta)$ $t = A \cdot m^2$      Washburn equation with
  t: time
  m: mass of the aspirated liquid $$A = \frac{\eta}{\{C \cdot \rho^2 \cdot \gamma \cdot \cos\theta\}}$$

η: viscosity of the liquid
ρ: density of the liquid
γ: surface tension of the liquid
θ: contact angle of liquid-powder
C: factor, only dependent on the geometrical properties of the powder and of the sample tube An illustration of the method of measurement is to be found in FIG. 5.

The surface energy GAMMA can be determined for particles as critical surface energy GAMMA-crit. by means of a Zisman plot which plots the respective contact angle THETA of the silica against a defined liquid, as determined above by the imbibition method, against the contact angle of the respective liquids.

However, for particles such as pyrogenic silica which form agglomerates having bulk densities $d_{SD} \ll 1$ g/ml but consist of primary particles having material densities $d_{MD} > 1$ g/ml, shaking into liquids of different surface tension can be used as a method: when wetting does not take place, the particle agglomerates float; in case of wetting, the air in the agglomerates is displaced and the particle agglomerates sink.

By using different liquids and different surface tension, the surface tension of a liquid at which the particle agglomerates sink can be exactly determined; this gives the critical surface energy $\gamma_{crit}$ as a measure of the surface energy γ of the particles.

The method can also be simplified in such a way that the surface tension of water (72.5 mN/m) is reduced by addition of methanol, ethanol or isopropanol.

Typically, water can be initially introduced, a certain amount of particle agglomerates laid (floating) on the water surface and the alcohol then added by titration, with stirring. The water-to-alcohol ratio on sinking of the particle agglomerates is noted and the surface tension is determined for this water:alcohol ratio exactly in a separate experiment using standard methods (ring detachment method, Wilhelmy method).

More effectively, and as carried out here, defined mixtures of water with methanol are prepared, and the surface tensions of these mixtures are then determined. In a separate experiment, these water:methanol mixtures are covered with a layer of defined amounts of particle agglomerates (for example in a volume ratio of 1:1) and shaken under defined conditions (for example, gentle shaking with the hand or using a tumble mixer for about 1 minute).

The water:methanol mixture in which the particle agglomerates just fail to sink and the water:methanol mixture having a higher methanol content, in which the particle agglomerates just sink, are determined. The surface tension of the latter methanol:water mixture gives the critical surface energy $\gamma_{crit}$ as a measure of the surface energy $\gamma$ of the particles, as shown in Table 1.

The dispersion fraction of the surface energy gamma-s-D is determined by using inverse gas chromatography and alkanes as probes, in line with "Inverse Gaschromatographie [Inverse gas chromatography]"-"Characterisation of Polymers and other Materials", 391 ACS Symposium Series, D R Lloyd, Th C Ward, H P Schreiber, Chapter 18, pages 248-261, ACS, Washington D.C. 1989, ISBN 0-8412-1610-X.

Preparation of an Aqueous Dispersion (Not According to the Invention)

18 g of the partly hydrophobic silica described above are predispersed in 82 g of demineralized water in a 500 ml stainless steel beaker by means of a dissolver having a toothed disk. The highly viscous but still flowable material obtained is pumped through an ultrasonic cell at a flow rate of 10 ml per minute and with an amplitude power of 300 watt. The analytical data of the dispersion thus obtained are summarized in Table 2.

TABLE 2

| Property | Aqueous dispersion from Example 1 |
|---|---|
| Solids content | 18.0% |
| pH | 5.2 |
| Mean diameter Sinter aggregates | 311 nm |
| Viscosity | 280 mPas |

Solids content of the dispersion determined by the following method: 10 g of aqueous dispersion are mixed with the same amount of ethanol in a porcelain dish and evaporated to constant weight in an $N_2$-flushed drying oven at 150° C. The mass $m_s$ of the dry residue gives the solids content according to solids content/%=$m_s$·100/10 g.

pH measured by means of a pH combination electrode mean diameter of the sinter aggregates measured by means of photocorrelation spectroscopy by the following method: 4 samples of the dispersion to be measured which have a silica content of 1% by weight, 0.75% by weight, 0.5% by weight and 0.25% by weight are prepared in demineralized water by stirring in the appropriate amount of starting dispersion by means of a magnetic stirrer. The samples are measured in a PCS apparatus Coulter N4 Plus from Coulter at detection angles of 30.1°, 62.6° and 90°. The mean diameter of the sinter aggregates is obtained by extrapolating the angle-dependent measured values obtained to a silica content of 0% and then averaging over the three measured angles.

Viscosity of the dispersion was determined using a rheometer MCR 600 from Haake with a cone-and-plate sensor system (105 µm measuring gap) at 25° C. and a shear rate D=10 s$^{-1}$.

Comparative Example

Preparation of an Emulsion (Not According to the Invention)

69.5 g of the above-described silica dispersion having a solids content of 18% by weight are initially introduced into a 500 ml stainless steel beaker. 150 g of a polydimethylsiloxane having a viscosity of 100 mPas (obtainable under the name "AK100" from Wacker-Chemie GmbH, Munich, Germany) are slowly metered in over a period of 15 min with stirring at 10,000 rpm using an Ultraturrax and while cooling with water. The temperature of the mixture should not exceed 60° C. 93 g of demineralized water are then slowly added over a period of 15 min, likewise at 10,000 rpm, to this now highly viscous stable material. The temperature of the mixture should not exceed 60° C. A low-viscosity white O/W emulsion results, the analytical data of which are summarized in Table 3.

Example 2

According to the Invention 69.5 g of a silica dispersion obtained according to Example 1, having a solids content of 18% by weight, are initially introduced into a 500 ml stainless steel beaker. 150 g of a polydimethylsiloxane having a viscosity of 100 mPas (obtainable under the name "AK100" from Wacker-Chemie GmbH, Munich, Germany) are slowly metered in over a period of 15 min with stirring at 10,000 rpm using an Ultraturrax and while cooling with water. The temperature of the mixture should not exceed 60° C. 93 g of demineralized water are then slowly added over a period of 15 min, likewise at 10,000 rpm, to this now highly viscous stable material. The temperature of the mixture should not exceed 60° C. 0.0035 g of NaCl are then added to the emulsion with stirring. A white O/W emulsion results, the analytical data of which are summarized in Table 3.

Example 3

According to the Invention 69.5 g of a silica dispersion obtained according to Example 1, having a solids content of 18% by weight, are initially introduced into a 500 ml stainless steel beaker. 150 g of a polydimethylsiloxane having a viscosity of 100 mPas (obtainable under the name "AK100" from Wacker-Chemie GmbH, Munich, Germany) are slowly metered in over a period of 15 min with stirring at 10,000 rpm using an Ultraturrax and while cooling with water. The temperature of the mixture should not exceed 60° C. 93 g of demineralized water are then slowly added over a period of 15 min, likewise at 10,000 rpm, to this now highly viscous stable material. The temperature of the mixture should not exceed 60° C. 0.022 g of NaCl are then added to the emulsion with stirring. A white O/W emulsion results, the analytical data of which are summarized in Table 3.

Example 4

According to the Invention 69.5 g of a silica dispersion obtained according to Example 1, having a solids content of 18% by weight, are initially introduced into a 500 ml stainless steel beaker. 150 g of a polydimethylsiloxane having a viscosity of 350 mPas (obtainable under the name "AK350" from Wacker-Chemie GmbH, Munich, Germany) are slowly metered in over a period of 15 min with stirring at 10,000, rpm using an Ultraturrax and while cooling with water. The temperature of the mixture should not exceed 60° C. 93 g of demineralized water are then slowly added over a period of 15 min, likewise at 10,000 rpm, to this now highly viscous stable material. The temperature of the mixture should not exceed 60° C. 0.088 g of NaCl are then added to the emulsion with stirring. A white O/W emulsion results, the analytical data of which are summarized in Table 3.

Example 5

According to the Invention 69.5 g of a silica dispersion obtained according to Example 1, having a solids content of 18% by weight, are initially introduced into a 500 ml stainless steel beaker. 150 g of a bisphenol A based epoxy resin having an average molar mass of <700 g/mol (obtainable under the name "Araldite GY 776 BD" from Vantico GmbH & Co KG) are slowly metered in over a period of 15 min with stirring at 10,000 rpm using an Ultraturrax and while cooling with water. The temperature of the mixture should not exceed 60° C. 93 g of demineralized water are then slowly added over a period of 15 min, likewise at 10,000 rpm, to this now highly viscous stable material. The temperature of the mixture should not exceed 60° C. 0.088 g of NaCl are then added to the emulsion with stirring. A white O/W emulsion results, the analytical data of which are summarized in Table 3.

Example 6

According to the Invention 69.5 g of a silica dispersion obtained according to Example 1, having a solids content of 18% by weight, are initially introduced into a 500 ml stainless steel beaker. 150 g of a polydimethylsiloxane having a viscosity of 100 mPas (obtainable under the name "AK100" from Wacker-Chemie GmbH, Munich, Germany) are slowly metered in over a period of 15 min with stirring at 10,000 rpm using an Ultraturrax and while cooling with water. The temperature of the mixture should not exceed 60° C. 93 g of demineralized water are then slowly added over a period of 15 min, likewise at 10,000 rpm, to this now highly viscous stable material. The temperature of the mixture should not exceed 60° C. 0.0416 g of CaCl2 are then added to the emulsion with stirring. A white O/W emulsion results, the analytical data of which are summarized in Table 3.

TABLE 3

|  | Comparative Example 1 | Example 2 | Example 3 | Example 4 | Example 5 | Example 6 |
|---|---|---|---|---|---|---|
| mmol/l electrolyte | 0 | 0.4 | 2.5 | 10 | 10 | 1 |
| Ionic strength/mol/l | $<10^{-6}$ | $4.0 \cdot 10^{-4}$ | $2.5 \cdot 10^{-3}$ | 0.01 | 0.01 | $3.0 \cdot 10^{-3}$ |
| Rel. viscosity $\eta_{rel}$ | 1 | 1.22 | 2.59 | 3.82 | 4.06 | 1.94 |
| tan δ | 2.0 | 0.29 | 0.17 | 0.13 | 0.15 | 0.20 |
| Conductivity μScm$^{-1}$ | 0 | 44 | 230 | 710 | 630 | 189 |
| Viscosity Pas | 0.129 | 0.158 | 0.335 | 0.465 | 0.427 | 0.361 |

Conductivity measured by means of conductivity measuring cell QCond 2400; correction of the measured value to $\Phi_w=1$ according to $\Omega_{corr}=\Omega_{meas}/\Phi_w$ Viscosity of the dispersion determined using an MCR 600 rheometer from Haake with a cone-and-plate sensor system (105 μm measuring gap) at 25° C. and a shear rate $D=10\ s^{-1}$ Loss factor tan δ of the dispersion determined using an MCR 600 rheometer from Haake with a cone-and-plate sensor system (105 μm measuring gap) at 25° C. by an oscillation experiment with variation of the shear stress amplitude from 0.05 Pa to 10 Pa at a constant angular velocity ω=6.28 rad/s at a volume fraction $\Phi_w$ of the water phase of 0.5 the relative viscosity $\eta_{rel}$ is defined as $\eta_{rel}=\eta/\eta_0$, where η is the absolute viscosity of the emulsion according to the invention and $\eta_0$ is the absolute viscosity of the starting emulsion at an ionic strength of $I \leq 1 \cdot 10^{-6}$ mol/l.

The invention claimed is:

1. An emulsion of the oil-in-water (O/W) type, containing:
   a) an oil disperse phase comprising a substantially water-insoluble component or optionally a plurality of substantially water-insoluble components,
   b) an aqueous phase,
   c) pyrogenic silica at an oil-water interface between the oil phase and the aqueous phase, the pyrogenic silica being partly silylated such that the content of non-silylated surface silanol groups on the silica surface is from not more than 95% to not less than 50% of the starting silica, or from 1.7 to 0.9 SiOH groups per nm² of silica surface, the dispersion fraction of the surface energy gamma-s-D being from 30 to 80 mJ/m² and the specific BET surface area being from 30 to 500 m²/g, d) an electrolyte content in the aqueous phase, which is set such that the ionic strength I of the solution is greater than $10^{-6}$ mol/l, where the ionic strength is defined as $I=\frac{1}{2} \cdot \Sigma c_i \cdot z_i^2$ where $c_i$ in this case is the concentration of the ion i in the solution, $z_i$ is the charge of the ion i, wherein the mean particle size of the disperse phase, measured by means of laser diffraction, is from 0.5 µm to 500 µm, wherein the emulsion is prepared by in a first step, a dispersion (1) of the partly silylated pyrogenic silica c) in a portion of the aqueous phase is prepared:

in a second step, a viscous preemulsion (2) is prepared by mixing the dispersion (1) with all the oil of the oil phase a), wherein the viscous preemulsion contains the total amount of partly-silylated pyrogenic silica contained in the oil-in-water emulsion: and in a third step, mixing in a remaining portion of the aqueous phase, wherein an electrolyte is added during at least one of steps (1) to (3) such that the oil-in-water emulsion has a viscosity greater than 1 mPa·s at a conductivity of the water-in-oil emulsion which is greater than or equal to 1 µS/cm, and wherein the electrolyte adjusts the viscosity of the oil-in-water emulsion to a viscosity higher than when the electrolyte is not present.

2. The emulsion of claim 1, wherein the water phase further comprises one or more water soluble organic compounds.

3. The emulsion of claim 1, wherein the electrolyte concentration is from $10^{-5}$ mol/l to 0.8 mol/l.

4. The emulsion of claim 1, wherein the conductivity is greater than 1 µs·cm$^{-1}$.

5. The emulsion of claim 1, wherein the electrolyte is an alkali metal salt or alkaline earth metal salt.

6. The emulsion of claim 5, wherein the electrolyte is a sodium or calcium salt.

7. A coating material, adhesive or sealant which contains an oil-in-water emulsion of claim 1.

8. A cleaning or cleansing agent which contains an oil-in-water emulsion of claim 1.

9. A water repellent, adhesion promoter, release agent, paper coating or foam control agent which contains an oil-in-water emulsion of claim 1.

10. A W/O/W or O/W/O multiple emulsion which contains an oil-in-water emulsion of claim 1.

11. The oil-in-water emulsion of claim 1, wherein the electrolyte is a water soluble inorganic compound.

12. The oil-in-water emulsion of claim 1, wherein the electrolyte is selected from the group consisting of water soluble halides, nitrates, nitrites, sulfates, sulfites, phosphates, and phosphites of metals of the $1^{st}$ to $4^{th}$ main group of the periodic table.

13. The oil-in-water emulsion of claim 1, wherein the electrolyte is present in an amount such that the ionic strength is greater than $10^{-4}$ mol/l to about 0.8 mol/l.

14. A process for the preparation of an oil-in-water emulsion of claim 1 of a targeted viscosity, comprising:

in a first step, preparing a dispersion (1) of the partly silylated silica in a portion of the aqueous phase;

in a second step, preparing a viscous preemulsion (2) by mixing the dispersion (1) with all the oil of the oil disperse phase, wherein the viscous preemulsion (2) contains all the partly silylated silica of the oil-in-water emulsion; and in a third step, mixing in a remaining portion of the aqueous phase; and adding in at least one of the first through third steps, an amount of an electrolyte to raise the viscosity of the oil-in-water emulsion to the targeted viscosity, the electrolyte being present in an amount greater than $10^{-6}$ mol/l.

15. The process of claim 14, wherein the electrolyte is present in an amount such that the ionic strength is greater than $10^{-4}$ mol/l to about 0.8 mol/l.

16. The process of claim 14, further comprising adding a filler, and then adjusting the viscosity of the emulsion containing the filler by addition of a soluble electrolyte to the aqueous phase.

* * * * *